United States Patent
Kaplan et al.

(10) Patent No.: US 8,512,221 B2
(45) Date of Patent: Aug. 20, 2013

(54) AUTOMATED TREATMENT SYSTEM FOR SLEEP

(75) Inventors: Kaplan Frederic Kaplan, Lakewood, OH (US); Kenneth Alan Loparo, Chesterland, OH (US); Ying Wang, Richmond Heights, OH (US)

(73) Assignee: Consolidated Research of Richmond, Inc., Euclid, OH (US)

( * ) Notice: Subject to any disclaimer, the term of this patent is extended or adjusted under 35 U.S.C. 154(b) by 226 days.

(21) Appl. No.: 12/639,201

(22) Filed: Dec. 16, 2009

(65) Prior Publication Data

US 2010/0094103 A1    Apr. 15, 2010

Related U.S. Application Data

(63) Continuation of application No. 10/790,885, filed on Mar. 1, 2004, now Pat. No. 7,654,948.

(60) Provisional application No. 60/451,055, filed on Feb. 28, 2003.

(51) Int. Cl.
*A61M 21/00* (2006.01)
(52) U.S. Cl.
USPC ............................................. 600/26
(58) Field of Classification Search
USPC ............... 600/26, 300, 500, 509, 544, 484, 600/535, 564, 575, 301; 379/373.01; 368/12, 368/107; 362/231; 340/573.1, 575; 128/204.23, 204.21, 204.26, 897, 898; 607/2, 607/46

See application file for complete search history.

(56) References Cited

U.S. PATENT DOCUMENTS

| | | |
|---|---|---|
| 4,228,806 A | 10/1980 | Lidow |
| 4,354,505 A | 10/1982 | Shiga |
| 4,550,736 A | 11/1985 | Broughton et al. |
| 4,617,525 A | 10/1986 | Lloyd |
| 4,776,345 A | 10/1988 | Cohen et al. |
| 5,101,831 A | 4/1992 | Koyama et al. |
| 5,154,180 A | 10/1992 | Blanchet et al. |
| 5,176,145 A | 1/1993 | Ryback et al. |
| 5,197,489 A | 3/1993 | Conlan |
| 5,259,390 A | 11/1993 | MacLean |
| 5,280,791 A | 1/1994 | Lavie |
| 5,299,118 A | 3/1994 | Martens et al. |
| 5,479,939 A | 1/1996 | Ogino |
| 5,520,176 A | 5/1996 | Cohen |

(Continued)

FOREIGN PATENT DOCUMENTS

| | | |
|---|---|---|
| EP | 0733504 | 9/1996 |
| JP | 08-299443 | 2/1991 |

(Continued)

OTHER PUBLICATIONS

Riley, W. at al., "Initial Evaluation of a Computerized Behavioral Intervention for Primary Insomnia", paper presented at the 36th Annual Convention of the Association for the Advancement of Behavior Therapy, Reno NV (Nov. 2002).

(Continued)

*Primary Examiner* — Samuel Gilbert
(74) *Attorney, Agent, or Firm* — Lane Powell PC; Priya Sinha Cloutier

(57) ABSTRACT

Automated behavioral methods and systems for treating Insomnia that use passive means for determining wake/sleep states.

30 Claims, 5 Drawing Sheets

(56) References Cited

U.S. PATENT DOCUMENTS

| | | | |
|---|---|---|---|
| 5,573,013 | A | 11/1996 | Conlan |
| 5,588,425 | A | 12/1996 | Sackner et al. |
| 5,724,990 | A | 3/1998 | Ogino |
| 5,732,696 | A | 3/1998 | Rapoport et al. |
| 5,813,993 | A | 9/1998 | Kaplan et al. |
| 5,816,247 | A | 10/1998 | Maynard |
| 5,846,206 | A | 12/1998 | Bader |
| 5,902,255 | A | 5/1999 | Ogino |
| 5,917,415 | A | 6/1999 | Atlas |
| 5,928,133 | A * | 7/1999 | Halyak ............................ 600/26 |
| RE36,450 | E | 12/1999 | Musha |
| 5,999,846 | A | 12/1999 | Pardey et al. |
| 6,067,019 | A | 5/2000 | Scott |
| 6,070,098 | A | 5/2000 | Moore-Ede et al. |
| 6,078,549 | A | 6/2000 | Wyatt et al. |
| 6,157,857 | A | 12/2000 | Dimpfel |
| 6,167,298 | A | 12/2000 | Levin |
| 6,171,258 | B1 | 1/2001 | Karakasoglu et al. |
| 6,239,706 | B1 | 5/2001 | Yoshiike et al. |
| 6,272,378 | B1 | 8/2001 | Baumgart-Schmitt |
| 6,317,627 | B1 | 11/2001 | Ennen et al. |
| 6,322,515 | B1 | 11/2001 | Goor et al. |
| 6,353,396 | B1 | 3/2002 | Atlas |
| 6,381,481 | B1 | 4/2002 | Levendowski et al. |
| 6,392,962 | B1 * | 5/2002 | Wyatt ............................ 368/107 |
| 6,468,234 | B1 | 10/2002 | Van der Loos et al. |
| 6,496,724 | B1 | 12/2002 | Levendowski et al. |
| 6,497,658 | B2 | 12/2002 | Roizen et al. |
| 6,511,424 | B1 | 1/2003 | Moore-Ede et al. |
| 6,575,902 | B1 | 6/2003 | Burton |
| 6,625,485 | B2 | 9/2003 | Levendowski et al. |
| 2001/0028309 | A1 | 10/2001 | Torch |
| 2001/0031930 | A1 | 10/2001 | Roizen et al. |
| 2002/0005784 | A1 | 1/2002 | Balkin et al. |
| 2002/0029005 | A1 | 3/2002 | Levendowski et al. |
| 2002/0067273 | A1 | 6/2002 | Jaques et al. |
| 2002/0082513 | A1 | 6/2002 | Ennen et al. |
| 2002/0183644 | A1 | 12/2002 | Levendowski et al. |
| 2003/0181821 | A1 | 9/2003 | Greenwald et al. |

FOREIGN PATENT DOCUMENTS

| | | |
|---|---|---|
| JP | 03-041926 | 11/1996 |
| JP | 09-225034 | 9/1997 |
| JP | 09-294731 | 11/1997 |
| WO | WO 9307804 | 4/1993 |

OTHER PUBLICATIONS

"Advanced Brain Monitoring,LLC Announces New Research Program to Identify Indices of Alertness", PR Newswire (Aug. 10, 1999).

"Interpreting the Brain", "Technologies, Products, and Market Applications—EEG", "Drowsiness Monitoring Device", "Patented Sensor Headset", Advanced Brain Monitoring, Inc., Home Page www.b-alert.com (2002).

Sadeh, A et. Al., "The Role of Actigraphy in the Evaluation of Sleep Disorders" Sleep (May 1995); (18(4);228-302.

Dircxx, J., "Wake Me When It's Over: Sleep and Its Disorders", Perspectives (Spring 2000), 28-35.

Xin, P. et. al, "Habituation of Sleep to Road Traffic Noise Assessed by Polygraphy and Rating Scale", Journal of Occupational Health (2000); 42:20-26.

Eiken, T., "Equipment and Facility Considerations: Establishing a Sleep Disorders Center", AACRC Times (May 1999), 35-38.

Craig, C., "Introduction to Sleep Disorders", HealthyInfo.com, www.healtyinfo.com (2002).

Portas, C. et. al., "Auditory Processing Across the Sleep-Wake Cycle: Simultaneous EEG and MRI Monitoring in Humans", Neuron (Dec. 2000), 28(3):991-999.

Principles and Practice of Sleep Medicine, Third Edition, Eds. Kryger. M. et. al. Philadelphia, PA, W.B. Saunders Company (2000).

Bootzin, R. Behavioral Modification and Therapy—An Introduction, Cambridge, MA, Wintrhrop Publishers (1975).

Lacks, P. Behavioral Treatment for Persistent Insomnia, Pergamon Books, Inc (1987).

Yang, C., "Insomnia", American Academy of Neurology—Continuum 8(6), Lippincott Williams & Wilkins, American Academy of Neurology (2002).

"Table DP-1: Profile of General Demographic Characteristics for the United States: 2000", United States Census 2000, US Census Bureau.

Bootzin, R. et. al., "Stimulus Control" Treatment of Late-life Insomnia, Eds. Lichstein, K et. al., Thousand Oaks, CA, Sage Publications (2000_.

Bootzin, R. et. al., "Sleep Disorder" Comprehensive Handbook of Psychopathology, Third Edition, Eds. Sutker P. et. al., New York, Kluwer Academic/Plenum Publishers (2001).

Bootzin, R. et. al., "Behavioral Treatments for Insomnia" Progress in Behavior Modification, vol. 6, Eds. Hersen, M. et. al., New York, NY: Academic Press, Inc. (1978).

Dorsey, C. et al., "Subjective Psychophysiologic Insomnia: An Examination of Sleep Tendency and personality" Biological Psychiatry (Jan. 15, 1997), 41(2):209-216.

Espie, C. et. al. "Substituting Behavioral Treatment for Drugs in the Treatment of Insomnia: An Exploratory Study", Journal of behavior Therapy & Experimental Psychiatry (Mar. 1988); (19(1):51-56.

Hauri, P., "Treating Psychophysiologic Insomnia with Biofeedback", Archives of General Psychiatry (Jul. 1981); 38(7):752-758.

Hauri, P., "Consulting About Insomnia: A Method and Some Preliminary Data", Sleep (Jun. 1993), 16(4):344-350.

Morin, C. et. al., Nonpharmacologic Treatment of Chronic Insomnia: An American Academy of Sleep Medicine Review, Sleep (Dec. 1999); 22(8):1134-(1156).

Engle-Friedman, M. et. al., "An Evaluation of Behavioral Treatments for Insomnia in the Older Adult", Journal of Clinical Psychology (Jan. 1992); 48(1):77-90.

Bootzin, R. et. al., "Nonpharmacologic Treatments of Insomnia", journal of Clinical Psychiatry (Jun. 1992), 53(Supp.):37-41.

Sloan, E. et. al., "The Nuts and Bolts of Behavioral Therapy for Insomnia", Journal of Psychosomatic Research (1993, 37(Supp. 1):19-37.

"2002 'Sleep in America' Poll" (Mar. 2002), National Sleep Foundation.

Adachi, Y., "Behavioral Treatment of Chronic Insomnia" Seishin shinkeigaku zasshi=Psychiatria et neurologia Japonica (2002)I 104(6):513-528.

Moric, C. et. al., "Behavioral and Pharmacological Therapies for Late-Life Insomnia: Randomized Control Trial" JAMA: The Journal of the American Medical Association (Mar. 17, 1999); 281(11):991-999.

Hajak, G. et. al., "As needed' Pharmacotherapy Combined with Stimulus Control Treatment in Chronic Insomnia—Assessment of a Novel Intervention Strategy in a Primary Care Setting" Annals of Clinical Psychiatry: Official Journal of the American Academy of Clinical Psychiatrists (Mar. 2002); 14(1):1-7.

Moric, C. et. al, "Behavioral and Pharmacological Therapies for Late-life Insomnia: A randomized Controlled Trial" JAMA: The Journal of the American Medical Association (Mar. 17, 1999):281(11):991-999.

Vincent, N. et. al., "Treatment Preference and Patient Satisfaction in Chronic Insomnia" Sleep (Jun. 15, 2001; (24(4):411-417.

Edinger, J. et. al., "Cognitive Behavioral Therapy for Treatment of Chronic Primary Insomnia: A Randomized Controlled Trial" JAMA: The Journal of the American Medical Association (Apr. 11, 2001); 285(14);1856-1864.

Morin, C., "Nonpharmacologic Treatment of Chronic Insomnia. An American Academy of Sleep Medicine Review" Sleep (Dec. 15, 1999); 22(8); 1134-1156.

Chesson, A. et. al., "Practice Parameters of the Nonpharmacologic Treatment of Chronic Insomnia. An American Academy of Sleep Medicine Report. Standards of Practice Committee of the American Academy of Sleep medicine" Sleep (Dec. 15, 1999); 39)5):688-696; Quiz 713-714.

Kirkwood, C., "Management of Insomnia", Journal of the American Pharmaceutical Association (Washington, DC: 1996) (Sep.-Oct. 1999); 39(5):688-696; Quiz 713-714.

"Practice Parameters for the Use of Polysomnography in the Evaluation of Insomnia. Standards of Practice Committee of American Sleep Disorders Association." Sleep (Jan. 1995);(8(1):55;57.

Morin, C. "Cognitive-behavior Therapy for Late-life Insomnia", Journal of Consulting and Clinical Psychology and Aging (Jun. 1992);7(2);282-289.

Edinger, J. et. al., "A Cognitive-behavioral Therapy for Sleep-Maintenance Insomnia in Older Adults", Psychology and Aging (Jun. 1992);7(2);282-289.

Friedman, L. et. al., "A Preliminary Study Comparing Sleep Restriction and Relaxation Treatments for Insomnia in Older Adults", Journal of Gerontology (Jan. 1991); 46(1):P1-8.

Idogawa K. et al., "A Time Variation of Professional Driver's EEG in Monotonous Work", Proceedings of the 11th Annual Conference of the IEEE Engineering in Medicine & Biology Society, 1989, p. 719-720.

* cited by examiner

AUTOMATED TREATMENT SYSTEM FOR SLEEP

CROSS-REFERENCE TO RELATED PATENT APPLICATIONS

This application is a continuation of U.S. application Ser. No. 10/790,885, filed on Mar. 1, 2004, now U.S. Pat. No. 7,654,948. U.S. application Ser. No. 10/790,885 claims priority to U.S. Provisional Patent Application No. 60/451,055 filed Feb. 28, 2003. This application incorporates U.S. application Ser. Nos. 10/790,885 and 60/451,055, in their entirety, herein by reference.

FIELD OF THE INVENTION

This invention is directed generally to helping people suffering from Insomnia and, more particularly, to highly effective automated systems for treating Insomnia that use passive methods of determining the wake and sleep states.

BACKGROUND

Insomnia is a complaint that sleep is difficult to initiate or maintain, or that it is not refreshing or restorative. A person that suffers from Insomnia has difficulty falling asleep or staying asleep, or wakes too early. As a consequence, Insomnia sufferers begin to dread not only each night of sleeplessness but also the fatigue, mental clouding, and irritability of the coming day.

Insomnia is a widespread problem. For example, a study conducted in the United States revealed that more than 50% of the respondents reported having experienced at least one of the following symptoms of Insomnia at least a few nights a week: difficulty falling asleep, waking often during the night, waking up too early and not being able to get back to sleep, and waking up feeling unrefreshed. In fact, 35% of the respondents said that they experienced at least one of these four symptoms of Insomnia every night or almost every night. Extrapolating these study statistics to the United States Census data at the time the study was conducted suggests that over 120 million U.S. adults experience at least one of the four symptoms of Insomnia at least a few nights every week. Of this 120 million, over 70 million experience these symptoms every night or almost every night. The direct economic costs of Insomnia in the U.S. are estimated at close to $14 billion annually. The amount spent on over the counter medications and "alternative" treatments such as herbal remedies may double this estimate.

Nonpharmacologic Behavioral Therapies have achieved significant success in treating Insomnia. Behavioral Therapies have many advantages over pharmacologic therapies, including:

No risk of tolerance, dependence or side effects.
Correcting core behavior instead of treating symptoms.
Documented safety and effectiveness.

There are a number of nonpharmacologic Behavioral Therapies that have been found to be effective for the treatment of Insomnia. Those that have been most extensively evaluated are Stimulus Control Therapy, Sleep Restriction Therapy, Relaxation Training and Paradoxical Intention. Thus far, among these therapies, no techniques have been found to be more effective than Stimulus Control Therapy.

Stimulus Control Therapy is based on the premise that Insomnia is a conditioned response to temporal (bedtime) and environmental (bed/bedroom) cues that are usually associated with sleep. Accordingly, the main objective of Stimulus Control Therapy is to re-associate the bed and bedroom with rapid sleep onset by curtailing overt and covert sleep incompatible activities that serve as cues for staying awake and by enforcing a consistent wake and sleep schedule. Stimulus Control Therapy may be characterized as consisting of the following instructional procedures:

1. Use the bed and bedroom only for sleep (sexual activity is the only exception to this rule);
2. When you get into bed, turn out the lights with the intention of going right to sleep;
3. If you find yourself unable to fall asleep within a brief period of time (e.g. 15 to 20 minutes), then get out of bed and leave the bedroom. Stay up as long as you wish and then return to the bedroom when ready to sleep;
4. If you still cannot fall asleep, repeat step 3. Do this as often as is necessary throughout the night;
5. Maintain a regular wake time in the morning regardless of sleep duration the previous night, and
6. Avoid daytime napping.

Another nonpharmacologic behavioral approach to treating Insomnia, Sleep Restriction Therapy, consists of curtailing the amount of time spent in bed to more nearly match the subjective amount of time asleep. For example, if a person reports sleeping an average of 5 hours per night out of 8 hours spent in bed, the initial prescribed sleep window (i.e., from bedtime to arising time) would be 5 hours. Subsequently, the allowable time in bed is increased by 15-20 minutes for a given week when average sleep efficiency (ratio of total sleep time to the total time spent in bed) exceeds 0.9, decreased by the same amount of time when average sleep efficiency is lower than 0.8, and kept stable when sleep efficiency falls between 0.8 and 0.9. Adjustments are made periodically (usually on a weekly basis) until the desired sleep duration is achieved. Sleep Restriction Therapy promotes rapid sleep onset, high sleep efficiency, and low inter-night variability. Also, to prevent excessive daytime sleepiness when implementing sleep restriction therapy, it is generally recommended that time in bed should not be less than 5 hours per night.

Behavioral techniques for treating Insomnia that utilize self-assessment of sleep parameters (such as sleep onset latency, total time asleep, total time awake after sleep onset, sleep efficiency, etc.) could be significantly enhanced if the burden of consciously keeping track of sleep parameters was relegated to an automated system. For example, with current approaches to Sleep Restriction Therapy, it is necessary for the user to be aware of the amount of sleep achieved each night and to record in a sleep journal or diary. The user or clinician would then use this journal or diary information to calculate average time asleep and average sleep efficiency for each week. Given the tendency for those with Insomnia to underestimate their time asleep, this could result in an overly restrictive sleep schedule, thereby reducing compliance by making the regimen less tolerable. Furthermore, the Sleep Restriction parameters would need to be regularly re-evaluated and updated as the user's sleep changes.

Central to the automation of Behavioral Therapies for Insomnia is the determination of sleep parameters. The determination of sleep parameters requires wake/sleep determination, that is, a determination as to whether the user is awake or asleep, as those terms are understood by those skilled in the art. The known techniques for determining wake/sleep states fall into two broad categories, determined from the perspective of the user, either active or passive. A device that relies upon the user to perform an action or be consciously aware in order to determine whether they are awake or asleep is considered an active device. An active device could require, for example, that the user respond to an audio tone with a button press or hold down the plunger of a dead mans switch in order to determine/infer whether the user is awake or asleep at any given instant in time. By contrast, a passive device would require no action on the part of the user in order to determine whether they are awake or asleep. A passive device, for example, could collect and analyze electroencephalographic (EEG) signals from the user to determine their wake and sleep states. Such a device would not require any action on the part of the user in making the wake and sleep determination.

There are advantages and disadvantages to both categories of devices. Probably the single biggest advantage of the active over passive devices is their relative simplicity. For example, monitoring the contact status of a dead mans switch (an active device) is much simpler and more straightforward than trying to determine changes in the wake/sleep state using EEG analysis (a passive device).

In 2002, Riley, W., et al., in an abstract entitled *Initial Evaluation of a Computerized Behavioral Intervention for Primary Insomnia* from the 36$^{th}$ Annual Convention of the Association for the Advancement of Behavior Therapy in Reno, Nev., described a behavioral therapy for Insomnia that required wake/sleep state information. Their approach used an active device that produced a low volume auditory beep every 10 minutes to which the user was required to respond. This presentation of the beep and the subsequent response (or lack thereof) was used to determine the wake/sleep state of the user. Active methods of wake/sleep determination, such as this, are not truly automatic and have many drawbacks, including the following:

(1) A continuous presentation of stimuli (beeps) can produce undue task loading of the user. If the user is tasked with responding to very frequent stimuli, then the device itself can interfere with the process of falling asleep. On the contrary, if the stimuli are presented too infrequently, then the time localization of the wake/sleep determination could become too inaccurate because of the temporal granularity. Long time intervals between successive stimuli provide an opportunity for the user to fall asleep but are at odds with the device's need for current information about the user's wake/sleep state. For example, with the presentation of successive stimuli every 10 minutes, the device does not know what happened during the intervening time; the user could have fallen asleep and awoken during the interval or at the presentation of the stimuli. This could negatively impact the implementation of a Behavioral Therapy.

(2) The stimuli used in the active device of Riley et al. has the potential of being missed by the user if it were presented at too low an amplitude. Similarly, the stimuli has the potential of waking the user if it were presented at too high an amplitude. Alternatively, an active device employing a small amplitude vibratory stimulus could be missed, and a large amplitude vibratory stimulus could wake the user. The same drawbacks apply to other types of stimuli used in other active devices.

(3) When using an active device, the user will be at a more heightened level of vigilance from being encumbered with having to perform a task. As a result, the user cannot simply relax in bed and passively rely on the device. Active devices can be especially detrimental to Insomniacs because sleep time for those with Insomnia tend to be more stressful than for people without sleep problems. While tasks required of anyone trying to fall asleep would have a negative impact on sleep, this is especially so in Insomniacs. Even a task as simple as depressing the plunger of a dead mans switch would necessitate a higher level of vigilance (i.e. making sure they continue holding down the switch) during a time when they should be relaxing and drifting off to sleep.

(4) Some active methods could awaken a bed partner, particularly if they use audible stimuli.

(5) Methods that employ switch contacts suffer from the inability to re-engage automatically when the user wakes. Because of this, they can typically only detect the first episode of sleep onset. A user suffering with Insomnia could also have trouble falling back to sleep after waking during the night, or, perhaps they may simply have trouble staying asleep. A dead mans switch, for example, would have to be re-engaged by the user in order for the device to re-determine the next period of sleep onset after waking. These methods would be extremely cumbersome to use for most normal sleepers and would be especially difficult for someone suffering from Insomnia.

Active wake/sleep determination methods have also been described for other applications including the following:

MacLean U.S. Pat. No. 5,259,390 describes a hand mounted vibrating stimulus-response device to monitor sleep behavior. This device is intended for in-home prescreening of sleep before a full polysomnogram is given. It determines wake and sleep states by requiring the user to press the response button each time they feel the vibratory stimulus.

Wyatt et al. U.S. Pat. No. 6,078,549 is directed to a sleep pattern timer using a plurality of switches to record parameters such as time before sleep onset, sleep time, etc. This device is used to assist in the diagnosis and treatment of sleep disorders by requiring the user to hold switch(s) in a closed position and then release when the user falls asleep.

Wyatt U.S. Pat. No. 6,392,962 entails a method of providing information to aid in the treatment of sleep disorders that would otherwise be difficult because of an Insomniac's underestimation of total sleep time and/or overestimation of the time necessary to fall asleep. The apparatus, which includes a wrist-mounted timer with a hand mounted actuator, stops timing when the Insomniac falls asleep and this disengages contact with the actuator. It is intended for wake/sleep determination (at sleep onset), and to correct an Insomniac's overestimation of sleep latency and underestimation of total sleep and sleep efficiency.

To the knowledge of the present inventors, passive methods of determining wake/sleep have not been used or suggested to automate the implementation of behavioral sleep therapies. Such passive methods can determine the wake/sleep state of the user without need of any action on the part of the user or the presentation of response inducing stimuli. Examples of devices that may be used to passively determine wake/sleep states (but do not teach or suggest automated behavioral therapy for Insomnia) include:

1) Blanchet et al. U.S. Pat. No. 5,154,180 (system to automatically determine sleep stage using an EEG);

2) Conlan U.S. Pat. No. 5,197,489 (system that can detect wake and sleep using an activity (or movement) monitor (actigraphy));

3) Lavie U.S. Pat. No. 5,280,791 (system that can determine the sleep state of a user by analyzing cardiac EKG R-R intervals);

4) Ogino U.S. Pat. No. 5,479,939 (device that can be used to determine between wake and sleep through a non-contact body movement sensor in bed);

5) Conlan U.S. Pat. No. 5,573,013 (system that can detect wake and sleep using an activity monitor (actigraphy));

6) Sackner et al. U.S. Pat. No. 5,588,425 (system that can be used to discriminate between sleep and wake in a monitored user based on systolic upstroke times in a pulse oximetry waveform);

7) Ogino U.S. Pat. No. 5,724,990 (device that can be used to distinguish between wake and sleep through a non-contact body movement sensor in a bed or seat);

8) Rapoport et al. U.S. Pat. No. 5,732,696 (system that uses multiple physiological signals (such as electroencephalography (EEG), electromyography (EMG) and electrooculography (EOG)) to score sleep);

9) Kaplan et al. U.S. Pat. No. 5,813,993 (to the present inventors) (system that tracks the state of a subject along a continuum of alertness, drowsiness, sleep, unconsciousness or anesthesia from a single channel of spontaneous EEG);

10) Bader U.S. Pat. No. 5,846,206 (system that estimates a person's wakefulness using a stationary pressure sensor in contact with that user's body);

11) Ogino U.S. Pat. No. 5,902,255 (device that can be used to distinguish between wake and sleep through a non-contact body movement sensor in a bed or seat);

12) Halyak U.S. Pat. No. 5,928,133 (device for waking a person within a preset time range when the user is, for all intents and purposes, already awake, using general technologies such as the use of "physiological monitoring means" or "measured electrical resistance" or "monitoring a bodily electrical property");

13) Pardey et al. U.S. Pat. No. 5,999,846 ("Insomnia or vigilance monitor" using an electrical signal from a user (EEG or otherwise) over a period of epochs, method for assigning a sleep stage type to each epoch using a neural network to determine wake and sleep in order to generate a hypnogram, a method for analyzing the hypnogram to generate a summary index of sleep quality and a method to display summary index of sleep quality based on the hypnogram;

14) Dimpfel U.S. Pat. No. 6,157,857 (system for sleep staging using the EEG);

15) Baumgart-Schmitt U.S. Pat. No. 6,272,378 (system to automatically generate a sleep stage classification using a single frontal EEG derivation using a device that stores a set of features (FFT based) from the incoming data (as a method of compression) and then analyzes these features to determine sleep stages using a neural network);

16) Goor et al U.S. Pat. No. 6,322,515 (system that is capable of determining sleep and wake by monitoring and detecting changes in peripheral arterial tone);

17) Van der Loos et al. U.S. Pat. No. 6,468,234 (sensor sheet that is laid on top of a conventional mattress for measuring the sleep quality of a user); and 18) Levendowski et al. U.S. Pat. Nos. 6,496,724, 6,625,485 and U.S. Publication No. 2002/0183644 (a system that quantifies the EEG along an alertness continuum).

Any of the above passive methods/devices for wake/sleep determination can be used in the practice of the present invention.

SUMMARY OF THE INVENTION

The invention described herein comprises a system for Behavioral Therapies for Insomnia that require knowledge of sleep parameters in their implementation. This system uses passive wake/sleep determination to achieve a truly automated system that does not require action on the part of the user being treated to produce information indicative of the user's wake/sleep state.

Thus, the present automated method utilizes passive wake/sleep determination means to produce information indicative of the user's wake/sleep state and implements the steps of Behavioral Therapy using this wake/sleep information as appropriate.

Behavioral Therapies for Insomnia comprises at least Stimulus Control Therapy, Sleep Restriction Therapy, Relaxation Therapy, Cognitive Behavior Therapy, or a combination thereof. While any Behavioral Therapy that utilizes information indicative of the user's wake/sleep state may be used, Stimulus Control Therapy, Sleep Restriction Therapy, and combinations of the two are preferred in the practice of the present invention. Also, while any passive wake/sleep determination means may be used, it is presently preferred that the determination means be chosen from among electroencephalography (EEG), electromyography (EMG), peripheral arterial tone (PAT), systolic upstroke time, electrocardiography (ECG/EKG), electrooculography (EOG), oximetry, heart rate variations, heart rhythm variations, actigraphy, body movement, galvanic skin response (GSR), respiratory changes, respiratory variability, eye movements, and combinations of two or more of these passive wake/sleep determination means. It will be obvious to a person having ordinary skill in the art that any means used to determine a user's sleep/wake state can be used with the present invention. EEG is the presently preferred sleep determination means.

Drug therapy may be used in conjunction with the Behavioral Therapy for Insomnia implemented according to the automated method of the invention. Also, active means for determining the wake/sleep state may be used to supplement the passive wake/sleep determination means.

In one important embodiment, a system according to the present invention would include: 1) means for powering on the system, 2) means for passive wake/sleep determination, 3) means for determining whether the user should get out of bed in accordance with the Behavioral Therapy rules, and 4) means for alerting the user to leave the bed if a determination is made according to the Stimulus Control Therapy rules that the user should get out of the bed.

In another important embodiment of the invention, a system is provided for treating users suffering from Insomnia including: 1) means for powering on the system, 2) means for determining whether the system is in a training mode, 3) means for passive wake/sleep determination, 4) means for determining whether the user has completed his/her sleep period, and if so, computing overnight sleep statistics, 5) means for calculating Sleep Restriction Therapy parameters based on previously-acquired sleep data, and 6) means for displaying the calculated Sleep Restriction Therapy program parameters for the upcoming sleep session.

DETAILED DESCRIPTION OF THE INVENTION

Figure 1:
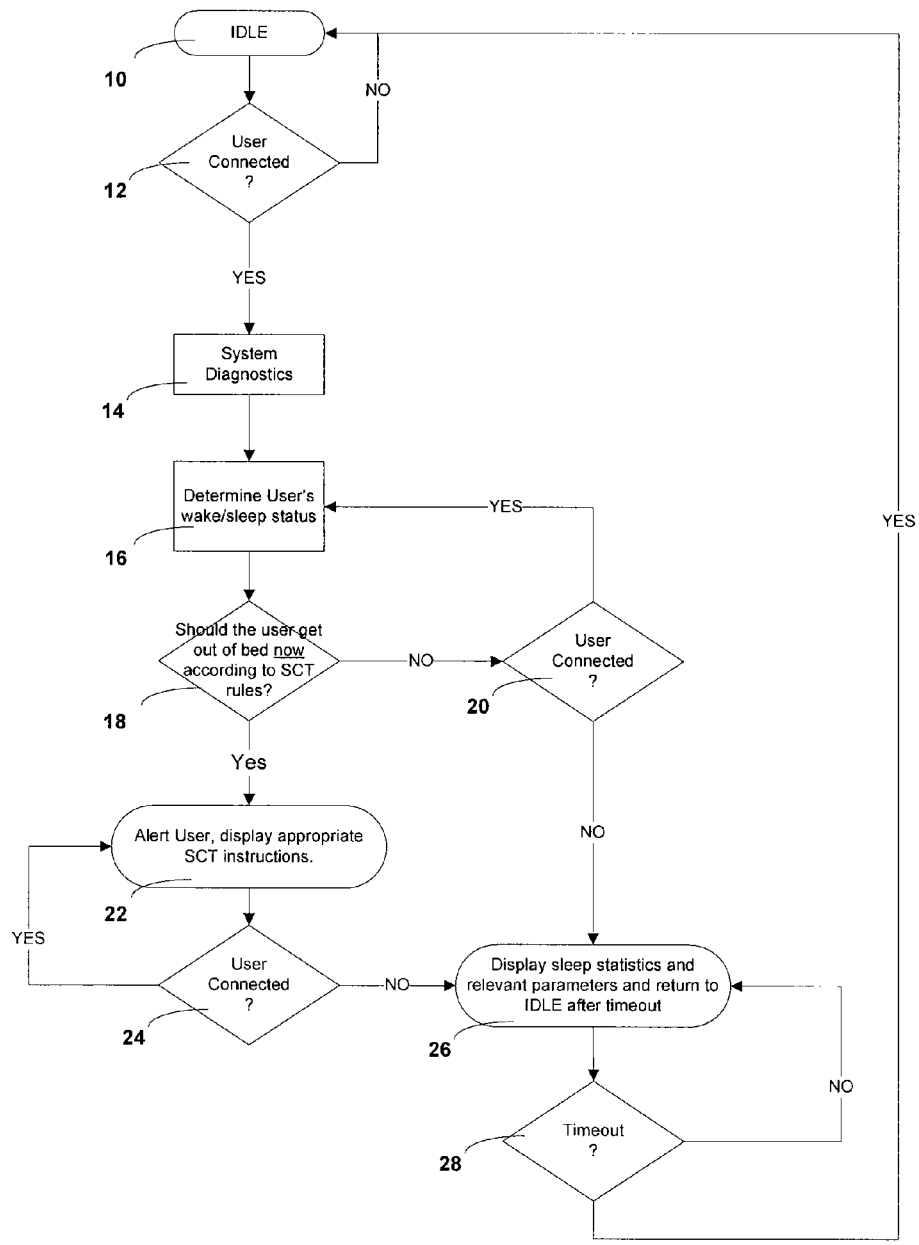
FIG. 1 is a flowchart presenting a high level overview of an automated implementation of Stimulus Control Therapy in accordance with the present invention.

In the description of the invention above, and in the detailed description of the invention, and the claims below, and in the accompanying drawings, reference is made to particular features (including method steps) of the invention. It is to be understood that the disclosure of the invention in this specification includes all possible combination of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The invention described herein employs passive wake/sleep determination means as part of an automated system for those implementing Behavioral Therapies for treating Insomnia that require knowledge of sleep parameters in their implementation. Such Behavioral Therapies include, for example, Stimulus Control Therapy, Sleep Restriction Therapy or a combination thereof.

In order to implement those Behavioral Therapies for treating Insomnia that require knowledge of sleep parameters in their implementation, it is necessary to determine if the user is awake or asleep at regular intervals of time. Highly accurate wake/sleep determination is desirable in order to achieve the best therapeutic results. Furthermore, being able to accurately determine the wake/sleep state continuously or at closely spaced time intervals is preferred over a coarse sampling of time. This may be achieved using passive wake/sleep determination means that use, for example, EEG, EMG, PAT, ECG/EKG, EOG, oximetry, heart rate variations, heart rhythm variations, actigraphy, body movement, systolic upstroke time, GSR, respiratory changes, respiratory variability, eye movements, or determination means that combine two or more of these modalities. However, it should be noted that it will be obvious to a person having ordinary skill in the art that other passive wake/sleep determination means, other than those described above, can be employed while still being within the scope of this invention. Also, while the focus of the present invention is on the automation of non-pharmacologic Behavioral Treatments of Insomnia, this inventive system may be employed where Drug Therapies are used in conjunction with Behavioral Therapies for the treatment of Insomnia. Finally, while passive techniques and devices for determining the wake/sleep state are always at the heart of the practice of the present system, active techniques and devices for determining the wake/sleep state may be used in a supplementary way at steps in the system where interference with sleep is not at issue.

EEG based wake/sleep state determination means are currently preferred in the practice of the invention. Such devices passively monitor the state of the user (awake or asleep). Because sleep originates in the brain and is controlled by the brain, the EEG signal provides a good information source for wake/sleep state determination.

Devices that determine wake and sleep by analyzing the information from movement/motion sensors (e.g. actigraphy) may also be used to passively detect wake/sleep states. Potential drawbacks to this type of device exist for users with highly disrupted or restless sleep, such devices could underestimate the time asleep. For the user with Insomnia that spends long periods of time in bed, lying very still, in an attempt to fall asleep, movement/motion-based monitors may overestimate the time asleep. However, it will be obvious to a person having ordinary skill in the art that, with appropriate signal processing technique, sufficiently accurate wake/sleep information could be obtained from movement/motion-based sensors for use in practicing the present invention. Such monitors may be obtained, for example, from Philips Respironics (United States), Actigraph (United States), and Ambulatory Monitoring, Inc. (United States), which sell a number of activity monitoring products.

Figure 2:
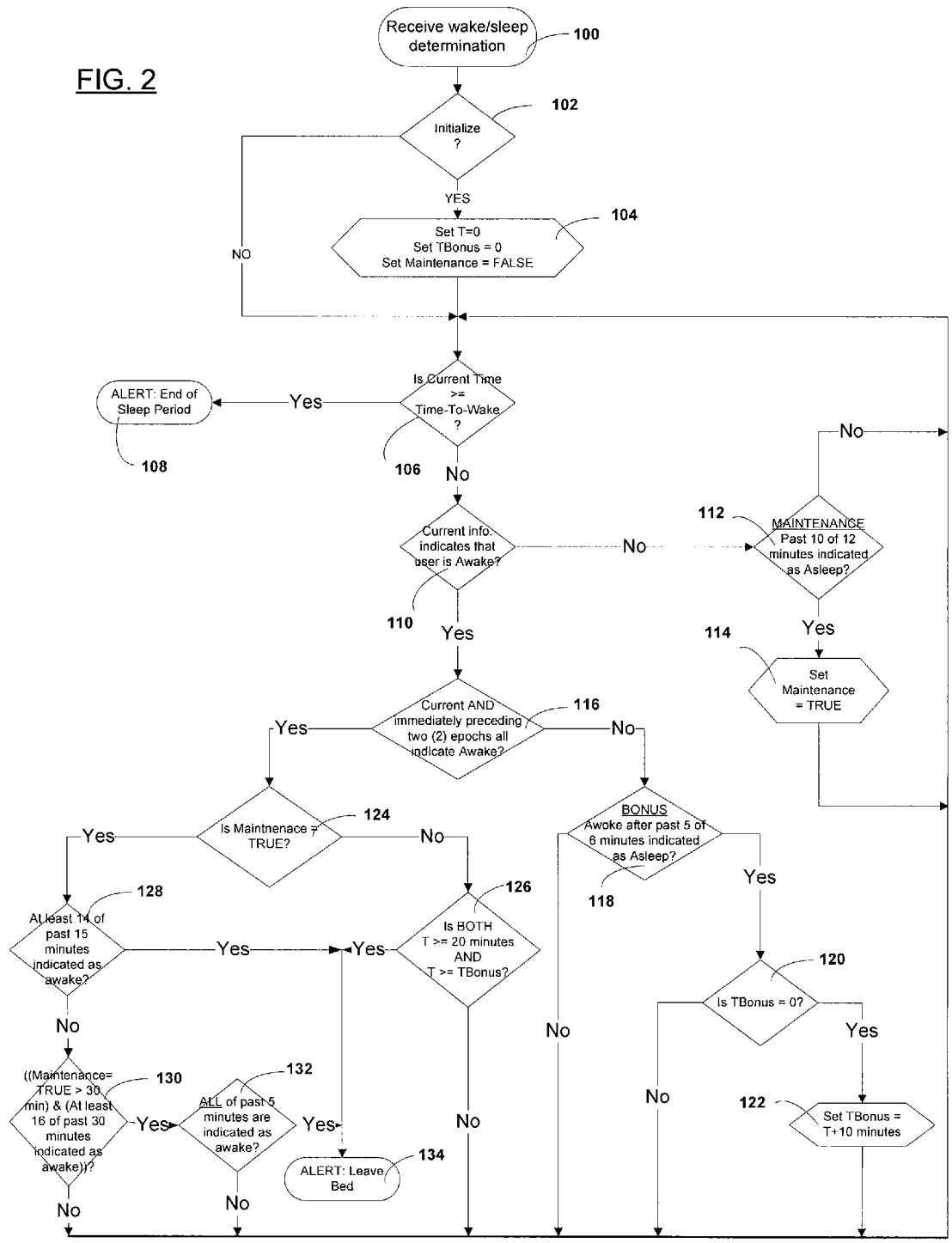
FIG. 2 is a flowchart presenting details of the automated implementation of Stimulus Control Therapy in accordance with the present invention.
Figure 3:
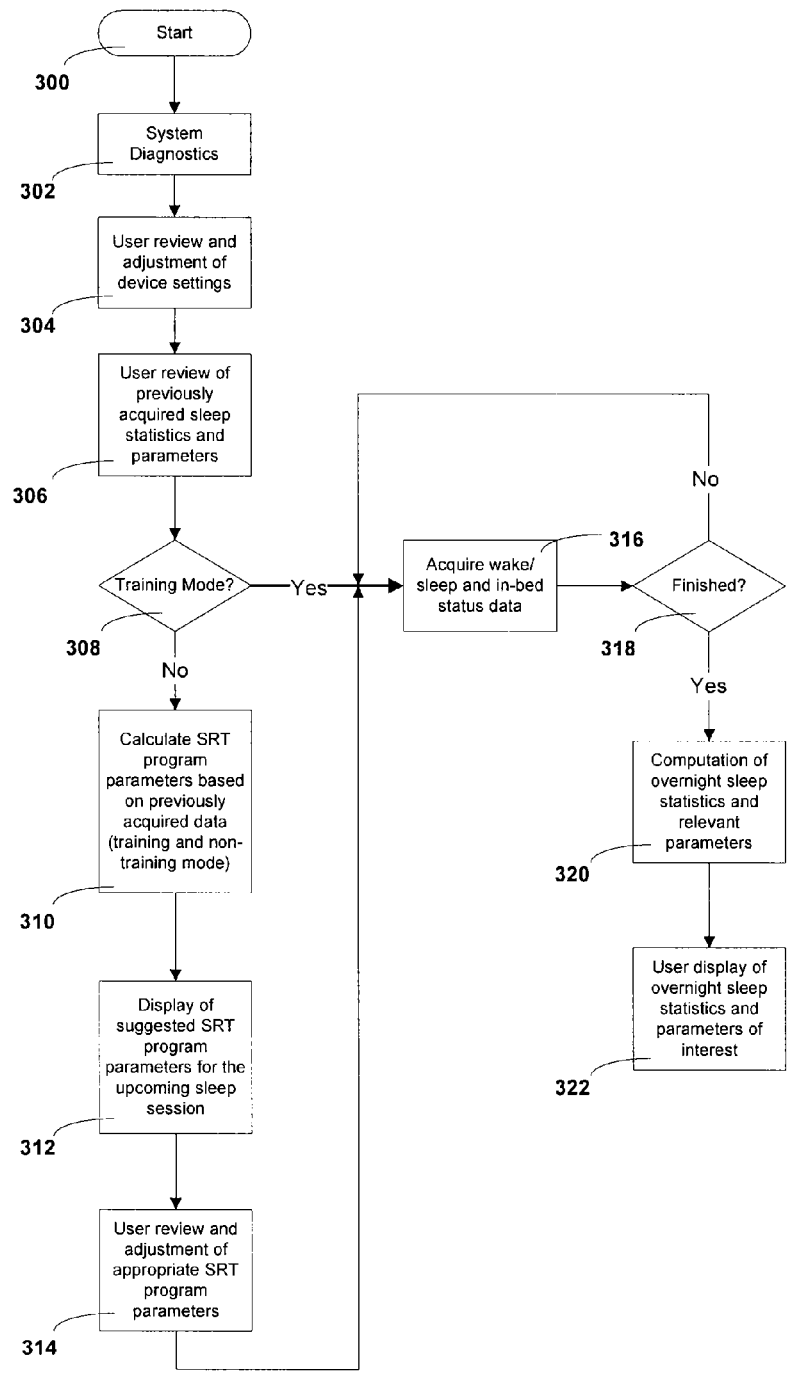
FIG. 3 is a flowchart presenting a high level overview of an automated implementation of Sleep Restriction Therapy in accordance with the present invention.

The implementation of Stimulus Control Therapy and Sleep Restriction Therapy requires following a set of guidelines and instructions. These guidelines and instructions can be represented in the form of a flowchart for each of the techniques. FIGS. 1, 2, and 3 demonstrate how each technique could be implemented in an automated system in accordance with the present invention. It will be obvious to a person having ordinary skill in the art that the implementation details described in the preferred embodiments can be varied while still being within the scope of the present invention.

Application to Stimulus Control

FIG. 1, a flowchart presenting a high-level overview of an automated implementation of Stimulus Control Therapy in accordance with the present invention, is discussed immediately below. Details and enhancements to the system overview are then presented in connection with the discussion of the flowchart of FIG. 2.

The system starts in IDLE mode (10), in which the system is essentially asleep and consumes little power. The check for a user connection of the EEG sensor cable is performed (12). When the EEG sensor cable is connected, the system leaves IDLE mode, otherwise the system remains in IDLE mode. When leaving IDLE mode, the system performs a diagnostic procedure (14) that may include: hardware self-test, software status, power status, EEG electrode impedances, etc. Errors and warnings are handled, logged and reported to the user as appropriate. Furthermore, when the EEG sensor cable is connected, the system may optionally produce a brief audible or tactile alert (depending on the user or clinician preferences) in the form of an audible chirp or short vibratory action and produce a Stimulus Control Therapy or other instruction such as "Try to sleep now. Do not do any other tasks such as work or reading,".

Following the system diagnostics (14), the system acquires EEG data and performs the necessary computations to determine whether the user is awake or asleep (16). These wake/sleep determinations could be made, for example, every 30 seconds.

After each wake/sleep determination, the system checks whether the user should be alerted to get out of bed in accordance with the automated rules for Stimulus Control Therapy (18).

If an alert is not indicated (18), and the user is still connected to the system (20), the system repeats the wake/sleep determination (16) every 30 seconds. If the user is no longer connected (20), then the system will stop EEG data acquisition and wake/sleep computation, and compute and display information that would be of interest or beneficial to the user (26), such as: time to sleep onset, total time in bed, total time spent asleep, total time spent awake, total time spent awake after sleep onset, number of awakenings, etc. The system will return to idle mode (10) after a pre-set display timeout is met (28).

If an alert is indicated (18), the system will produce an audible alert and present an appropriate message on the system display (22). The system may advise the user to stop trying to sleep now, leave the bed and bedroom, and return to bed when feeling tired enough to attempt sleep again. The alert would persist until the user has disconnected their EEG sensor cable (24) at which time the system will stop EEG data collection and wake/sleep computation, compute and display information that would be of interest to the user (26), such as: time to sleep onset, total time in bed, total time spent asleep, total time spent awake, total time spent awake after sleep onset, number of awakenings, etc. The system will return to idle mode (10) after a pre-set timeout is met (28).

Depending on user or clinician preferences, the Alert may be any one or more of a text display of the Alert condition, a text display of instructions or information, activation of the display backlight, a blinking light, an audible indication, a tactile indication, a synthesized or recorded voice, a low level electrical stimulus or even an aroma generated by an appropriate device. We refer to these alerts (as well as any other appropriate alerts) as "the Alert Set."

Although not detailed in the flow diagram, the system should continuously or periodically check for valid sensor signals and the integrity of the sensor connections.

The system depicted in FIG. 1 may also include the optional features as follows:

1. A display which, whenever the user is out of bed, displays data and summary statistics for the current recording period. For example, if the user gets out of bed in the middle of the night for some reason, the device may display the number of hours they have been asleep, the number of hours they have been in bed, their sleep efficiency thus far this night, the current or elapsed time, etc.

2. An alert to get out of bed may be maintained until the user actually gets out of bed. In the absence of an automatic in-bed sensor, the user would have to indicate to the device that they are out of bed (i.e. button press or disconnection of sensor cable) to stop the alert.

3. The presentation of (context sensitive) instructions and information on an appropriate display or by prerecorded or synthesized voice. For example, when the user is in bed and the device tells them to leave the bed, it would give appropriate instructions such as "leave the bed and bedroom, only return when ready to try to sleep". Or, when the user is out of the bed, it could tell them to "return/go to bed only when sleepy and ready to try to sleep". Or, when they first get into bed, it could tell them to "try to go directly to sleep, no reading or TV, turn the lights out", etc.

4. The system may include appropriate means to allow the user to specify a wake up time and act as an alarm clock to wake the user at a consistent time each morning.

5. The user could wear the device when out of bed and the device could monitor them for sleep outside of the bed and bedroom. This would help prevent napping which could adversely affect their Insomnia treatment.

Turning now to the flow diagram of FIG. 2, an example implementation of an automated implementation of Stimulus Control Therapy, in accordance with the present invention is shown. FIG. 2 could be interpreted as an expansion of FIG. 1 block 18. A wake/sleep determination is received (100). If this is the first wake/sleep determination following a user connection (102), the system initializes variables for Stimulus Control Therapy such as "T", "TBonus" and "Maintenance" (104), otherwise the system proceeds without initializing (106).

If the current time is at least the pre-determined wake-up time (106), then the system returns an ALERT indication (108). If the current time is less than the pre-determined wake-up time, then the system checks the user's EEG wake/sleep state (110). If the user is not awake, then the system checks the user's wake/sleep history to see if, during the last 12 minutes, the user was asleep for at least 10 of those minutes (112). If they were asleep for at least 10 of the last 12 minutes, then the Maintenance flag is set to true (114) and the system returns to 106. If they were not asleep for at least 10 of the last 12 minutes, then the system returns to 106. Otherwise, if the user is awake (110) (i.e. the most recent wake/sleep determination is wake), then the system checks (116) as to whether the last two wake/sleep determinations were both awake (i.e., this epoch and the one immediately preceding). If the user has not been awake for both epochs, then check the wake/sleep history (118) to determine whether, during the past 6 minutes, the user was asleep for at least 5 of those minutes. If they were not asleep for at least 5 of the past 6 minutes, then the system returns to 106. Otherwise, if they were asleep for at least 5 of the past 6 minutes, the system checks (120) whether TBonus is zero. If TBonus was zero, then TBonus is set to the current elapsed time plus 10 minutes (122) and returns to 106. This will effectively inhibit the alarm for an additional 10 minutes as a reward for achieving at least 5 minutes of relatively contiguous sleep. If TBonus was not zero, then the system returns to 106 (i.e., do not give a second bonus).

If the last two wake/sleep determinations were both awake (116), the system checks whether the Maintenance flag is true (124). If the Maintenance flag is true (124), then the system checks whether at least 14 of the past 15 minutes was indicated as awake (128). If at least 14 of the past 15 minutes was indicated as awake (128), then the system returns an alert indication (134). If there were not at least 14 of the past 15 minutes indicated as awake (128), then the system checks whether both the Maintenance flag has been true for greater than 30 minutes and whether at least 16 of the past 30 minutes are indicated as awake (130). If this is false (130), then the system returns to 106. If this is true (130), then the system checks whether all of the past 5 minutes were indicated as awake (132). If this is true (132), then return an alert indication (134). If this is false (132), then the system returns to 106. If the Maintenance flag is false (124), then the system checks whether both T is at least 20 minutes and whether T is at least TBonus (126). If this is true (126), then the system returns an alert indication (134). If this is false (126), then the system returns to 106.

Application to Sleep Restriction Therapy

FIG. 3 represents a high level overview of an implementation of Sleep Restriction Therapy in an automated device, in accordance with the present invention.

The system starts with power-on or connection of EEG electrodes (300). The system completes a diagnostic procedure (302) that may include: hardware, software, power, electrode/sensor status, etc. Errors and warnings should be handled as appropriate. Following diagnostics, there may be an opportunity for the user to make adjustments to system settings (304). On the first use of the device, these settings may be displayed for review by default. On subsequent use of the device, this menu may be optionally displayed or called up by the user or may be locked and only available to a clinician. These settings will include such items as setting the current time, age, sleep goals, alert preferences (audible, tactile or both), language, setup parameters, display preferences, backlight preferences, use of abbreviated messages, use of verbose messages, etc. Each time the device is started (or the user is connected, etc.) or stopped (or the user is disconnected, etc.), the system may display individual night or summary statistics and allow the use to review them as desired. Progress trends, etc. may also be displayed (306). This all falls under the category of user feedback.

The system may need to acquire sleep related parameters from the user for a number of nights before implementing the sleep restriction therapy program. Most experts currently use one week of subjective data to determine program parameters. In order to eliminate alteration of sleep due to the addition of this device, the first day or two of data may be eliminated from the calculation of program parameters. The system could automatically start in training mode (308) or the user could select training mode manually. If the system is in training mode (308), then the system will acquire wake/sleep data, the in-bed status (either derived manually or using automatic means), the time of each observation, etc. (316). These observations could be made every 30 seconds or at other desired intervals. If the data collection is finished (318), the recording will stop. The system will know that the data collection is finished either by the user manually indicating such to the device or when the electrodes/sensor cable is disconnected. When the data collection is completed, the system will compute the necessary sleep related parameters (320) and display them to the user (322). Parameters relevant to the Sleep Restriction Therapy program will be computed, such as total time asleep, total time in bed, sleep efficiency, etc. (320). If the night's data collection is not finished (318), the system will continue acquiring wake/sleep data, in-bed status, time of each observation, etc. (316).

If the system is no longer in training mode (308), the system will calculate the Sleep Restriction Therapy program parameters based on previously collected data (310). Parameters such as average number of hours asleep over the past week and average sleep efficiency over the past week will be calculated. The Sleep Restriction Therapy program parameters will be displayed to the user (312). The user may have the opportunity to change certain program parameters (314), after which the system will continue acquiring wake/sleep data, in-bed status, time of each observation, etc. (316). The system depicted in FIG. 3 may also include optional features as follows:

1. A step in which additional information is determined related to the time interval(s) corresponding to the highest likelihood of sleeping by looking at those time intervals when sleep is most often achieved. For example, consider a user that averages 5 hours of sleep per night, where sleep is concentrated between the hours of 3 to 6 AM on the majority of nights (this is the time interval when the user was most often asleep). The "standard" implementation of the sleep restriction therapy program would simply suggest that the user limit their time in bed to 5 hours per night. With this additional information, the device used to implement the system could further suggest that the user plan their 5 hours of sleep to coincide with the hours of 3-6 AM to further increase their chances of achieving sleep.

2. Going a step further, the device could trigger an alert when the user is getting close to this optimal time for sleeping. Obviously, the alarm could be inhibited if the user were already in bed.

3. The system could alert the user to leave bed once the user has been in bed for the recommended length of time. In the abovementioned example, the device would alert the user to leave bed after they have been in bed for 5 hours.

4. The system may include appropriate means to allow the user to specify a wake up time and act as an alarm clock to wake the user at a consistent time each morning. The user should have to ability the enable/disable or specify a new time as needed.

5. The user could wear the device when out of bed and the device could monitor them for sleep outside of the bed and bedroom. This would help prevent napping which could adversely affect their Insomnia treatment.

6. Whenever the user is out of bed, the device may display data and summary statistics for the current recording period. For example, if the user gets out of bed in the middle of the night for some reason, the device may display the number of hours they have been asleep, the number of hours they have been in bed, their sleep efficiency so far this night, the current or elapsed time, etc.

Implementation

Implementation of the system of the invention with any Behavioral Insomnia Therapy begins with the physical arrangement of the hardware of the passive monitoring modality to be used. Table 3 below identifies examples of possible wake/sleep determination means, which may be used with the present invention. Use of any of the passive monitoring modalities described in Table 3 should be performed in accordance with the device specifications. However, it will be obvious to a person having ordinary skill in the art that any means used determine the user's sleep/wake state can be used with the present invention.

TABLE 3

Passive Monitoring Modalities

| Modality | Attachment to User |
|---|---|
| EEG | (1) Electrodes located on the head, ideally located outside of the hairline to facilitate self application<br>(2) Ideally use pre-gelled self-stick electrodes<br>(3) Could also ensure electrode attachment using a mechanical fastener such as a headband |
| EMG | (1) Electrodes located at appropriate sites, preferably in a location that would be compatible with sleep<br>(2) Ideally use pre-gelled self-stick electrodes<br>(3) Could also ensure electrode attachment using a mechanical fastener |
| Actigraphy (activity or movement monitor) | (1) Could be worn on wrist, arm, ankle, leg, or otherwise body mounted according to the specifications of the device |
| Body movement sensor(s) | (1) Could be a contact device attached to the wearer according to the specifications of the device<br>(2) Could be a non-contact device mounted on the bed or a stationary object (pressure sensors, movement sensors)<br>(3) Could be a non-contact passive device (RF motion detector, ultrasonic motion detector, machine vision system to detect motion/movement) |
| Galvanic skin response | (1) Attached to a convenient location on the skin that is compatible with sleeping |
| Respiratory responses/ Respiratory variability | (1) Could use respiratory belts/bands<br>(2) Flow monitors (oral or nasal thermisters)<br>(3) Monitor breathing sounds using a contact or non-contact microphone or other audio transducer |
| EOG | (1) Electrodes to monitor eye movements can be mounted above and below the eyes or on the sides |
| Eye Movements (non-EOG) | (1) IR and/or microwave reflectance<br>(2) Machine vision system to watch the eyes (camera) |
| ECG/EKG/Heart Rhythm Variability | (1) Could use electrode locations on the chest to acquire the ECG/EKG<br>(2) Could use electrode locations on extremities (i.e., one on each wrist) to acquire the ECG/EKG |
| Peripheral Arterial Tone | (1) Could use an appropriate sensor to get peripheral arterial tone on an extremity. |
| Systolic Upstroke Time | (1) Could use a pulse-oximeter to get systolic upstroke times. |
| Pulse oximetry/ Heart Rhythm Variability | (1) Finger, toe, earlobes or other appropriate locations. |

Thus, for example, in the case of the body worn EEG device, the user would mount the device as appropriate to their body and attach the electrodes to their head, preferably outside the hairline using pre-gelled self-stick electrodes.

Then, for example, if Stimulus Control Therapy were selected (either manually selected by the user or automatically selected by the device), the user would go to bed when ready to try to sleep. The device would know that the user was in bed either through automatic sensing means or by the user indicating this to the device by a button press or by connection of the electrode cable.

The system then monitors the user and continuously tracks whether the user is awake or asleep by analyzing their EEG signals. Using this information, the device would follow the algorithmic flow indicated in FIG. 1 and FIG. 2 as discussed above. If the user fell asleep within the appropriate period of time and for at least the prescribed length of time, the device would passively monitor, while continuously collecting wake/sleep information, in-bed status and time, etc. If the Behavioral Treatment program dictated that the user should get out of bed, then the device would alert the user through an alarm chosen from the Alert Set. Preferably, the alarm type and intensity could be modified by the user or medical provider if the default values were not desirable. For example, someone using this device with a bed partner in close proximity may prefer a silent tactile alarm rather than an auditory alarm.

In response to the alert, the user would get out of bed and leave the bedroom until ready to sleep once again (as specified by the Stimulus Control Therapy program of the automated system). If the user remains in bed or does not leave the bedroom, the device could detect this behavior and alert the user that they are not following the program as intended. For those people whose living conditions or situation are such that leaving the bedroom is not feasible, the device could be set to relax this condition. When the user is ready to sleep once again according to the rules of the program (which may be written, but may also be displayed on the device display at the appropriate times or provided verbally), they would once again get back in bed to try to sleep. The unit could monitor continuously, whether in-bed or out of bed. If the unit detected sleep while the user was out of bed, then it could alert the user that this behavior is contraindicated and may reduce the effectiveness of the program. Sleep should be in the bed and bedroom only whenever possible. Since this behavioral therapy is a "reconditioning" program, the rules should be enforced whenever possible. Furthermore, the system could detect any awakenings and, if necessary, alert the user that they need to get out of bed.

As explained earlier, in the case of Stimulus Control Therapy, the user should only be in bed when trying to sleep. When they cannot sleep, they are instructed by the system to physically remove themselves from the bed and bedroom. This would necessitate the device knowing when the user was in the bed. A pressure transducer or motion sensor under the bed sheets could be used to sense whether the user was in bed (and presumably trying to sleep) or not. Or, the user could manually indicate to the device that they were ready to try and sleep by pressing a button on the device (the manual approach). This manual approach suffers from the possibility of the user forgetting to press the button and the device remaining inactive. If the device was body worn, then it could contain an RF receiver that picks up a very low power RF transmitted signal (beacon) placed in close proximity to their bed. The idea being, that when the user is in bed, they would be close enough for the body worn device to detect the low power transmitted signal (beacon) and automatically know that the user was in bed. Many other devices could also be used, such as temperature sensors to pick up body heat, etc. At present, however, a small RF transmitter is preferred, either placed directly under the bed, on the headboard, or on the nightstand and would not be prone to the false detection of a bed partner, pet, etc. Further, the device could presume that the user was in bed whenever they were connected to the device.

Passive sensors used to determine whether the user is in bed or not, such as a low power RF transmitter, could also be used to help ensure program compliance. In one mode of the invention, when the device alerts the user that they should get out of bed, the alarm (auditory and/or vibratory for example) could continue until the device has detected that the user has physically removed themselves from the bed and bedroom (i.e. out of the transmit range of the beacon). The radiated output of the RF beacon could be directional in nature. Furthermore, the power of the RF beacon could be user adjustable. This would allow the user to adjust the RF beacon so that the transmit pattern was coincident with the bed and bedroom area as much as possible.

Furthermore, the device could help ensure compliance that sleep only occurs in the bed. If a user were to fall asleep on a couch or chair (i.e. not in the bed and bedroom), the device could detect that sleep was occurring outside of the bed and bedroom and signal an alert. Ensuring that sleep occurs only in the bed/bedroom is another step in implementing good sleep hygiene and is part of the overall therapy.

The above illustrates use of the system when only wake and sleep information is available. If additional sleep staging information is available, then it is possible to implement more elaborate schemes. For example, the addition of stage-1 sleep information could enable the system to wake the user from sleep if that user has not progressed beyond stage-1 sleep within a prescribed interval of time (for example, 20 minutes).

Hardware for implementing the inventive system may take many different shapes and forms, such as those described below.

Stationary Devices

A tabletop device for implementing the inventive system could sit on the floor or nightstand next to the user's bed. EEG electrodes (or other appropriate sensors) would connect to a cable that would plug into the device. One disadvantage of this approach is that the user is tethered to a stationary device and it is possible for the wires to tangle or become an annoyance. However, routing the wires toward the top of the bed and then to the device usually solves this problem. When the user has to get out of bed (i.e. needs to use the bathroom, or because the device instructs them to do so) then they must disconnect themselves from the stationary device and can carry the electrode cable with them. Thus, a benefit of this approach is that the user must re-attach themselves to the device when back in bed and this would provide the necessary information for the device to start and stop without any other detectors or actions on the part of the user (i.e. this is essentially an automatic in-bed sensor by default). Finally, the device would not be able to continuously monitor the user when out of bed for any sleep outside of the bed and bedroom. If the tabletop device was powered from the wall outlet, then suitable power and ground isolation design techniques, well known in the art, must be employed to protect the user from any potential electrical hazard(s).

Semi-Stationary

A tabletop model, as described above, but using a wireless connection between the electrodes/EEG amplifiers and the stationary device, may also be used. In this case, the electrodes would plug into a small wireless EEG amplifier/transmitter that can be body worn to send signals to the tabletop device. This has the advantage of removing the mechanical tether between the user and a stationary object. It also provides inherent electrical isolation between the user and the tabletop device, since the transmitter worn by the user would most likely be battery powered. This also has the advantage of being used as an in-bed sensor if the transmitter were low power or had the ability to sense the distance from the transmitter to the base unit. If the transmitter were powerful enough, the device may be used for out of bed monitoring as well.

Body Wearable

The most desirable form of the hardware for implementing the present inventive system would have the entire device be body worn. In this case, the device is worn by the user and the electrodes plug directly into the device. The device would most likely be powered by batteries and would not need to be isolated from the wall outlet. This device would be simpler than the semi-stationary system described above as it would not need a sophisticated EEG transmitter/receiver pair. The user would also be un-tethered at all times, thereby making it preferable to the stationary device as described above. The body wearable device would also be able to monitor the user for out of bed sleep and prevent this from occurring.

This device would likely benefit from a wireless in-bed sensing device, such as a low power RF transmitter mounted near the bed as previously described. The body worn device would simply need to detect the beacon signal. A more sophisticated model would gauge the distance to the transmitter and know whether the user was in bed or just nearby. A pressure sensor under the bed sheet with a very low power RF transmitter optimally could also be used for in-bed detection. In a simple approach, however, the user may just press a button on the body worn device to indicate that they are in-bed and ready for sleep. Other device embodiments could sense light and movement and actively prompt the user as to whether they are now going to attempt sleep.

Figure 4:
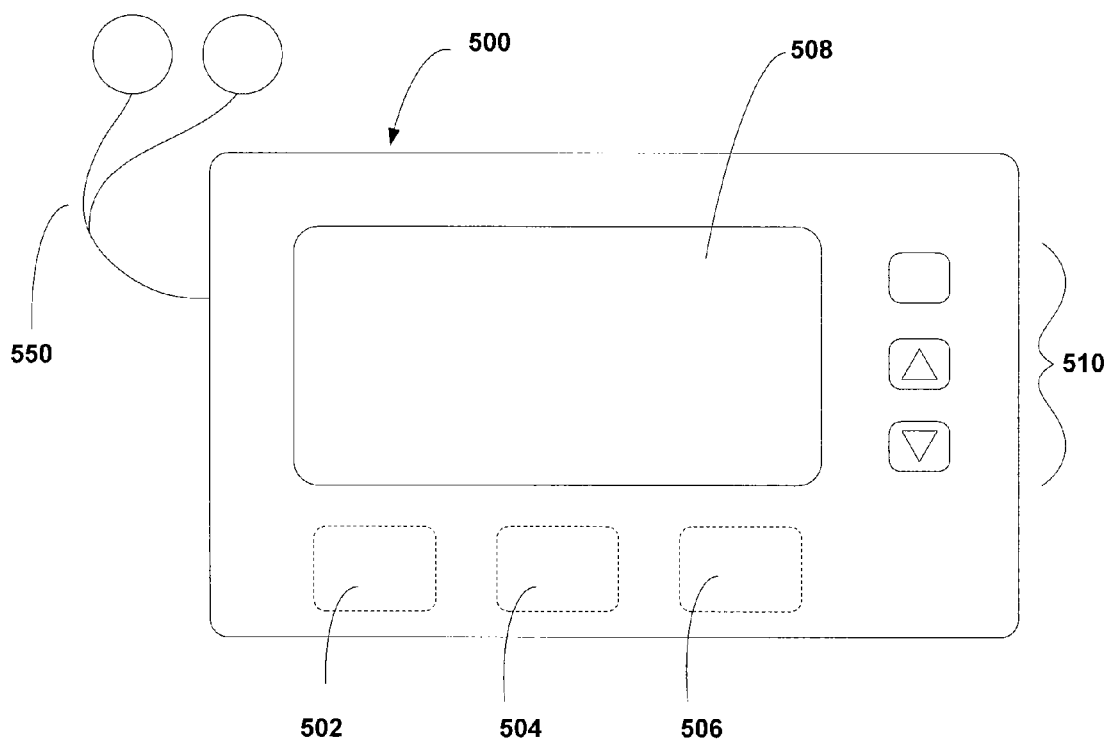
FIG. 4 is a diagrammatic representation of one possible body wearable device in accordance with the present invention.

One possible body wearable device (500) is depicted diagrammatically in FIG. 4. It may include visual (502,508), audible (504) and tactile alerts (506). A human machine interface output (508), such as an LCD could be provided. A human machine interface input (510), such as buttons for input and navigation may also be available.

An EEG based embodiment of the present system may be implemented using a body wearable device or otherwise, in which electrodes (550) are used as sensors on the person to be monitored.

Figure 5:
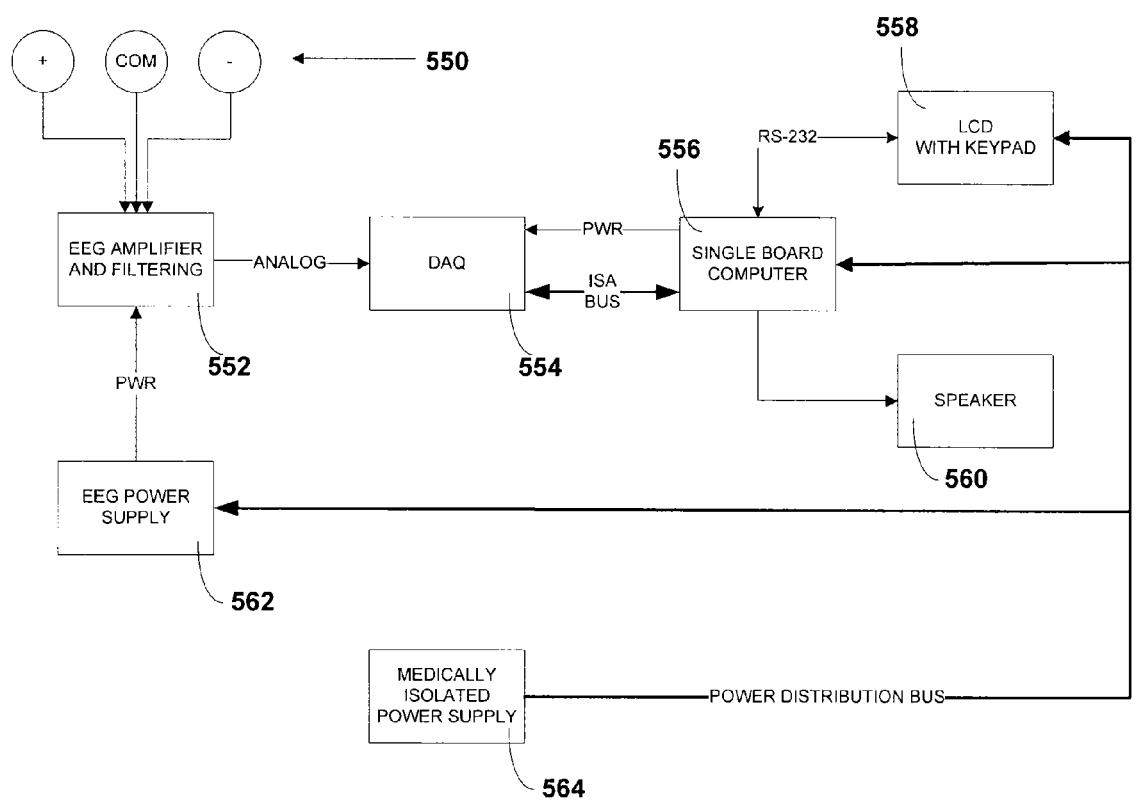
FIG. 5 is a block diagram representation of one possible stationary EEG-based embodiment in accordance with the present invention.

The block diagram of FIG. 5 represents the components of an EEG based embodiment of the present system in a stationary design that is capable of implementing wake/sleep determination as specified in U.S. Pat. No. 5,813,993 to the present inventors. While the algorithm described in this patent can be used for wake/sleep determination in the present invention, any other suitable passive wake/sleep determination means or algorithm could also be employed in its place.

Examples of components that could be used in the stationary design of FIG. 5 are described below. One skilled in the art could choose alternate components, while preserving the overall functionality, to build a body wearable design. For example, in such a body wearable design, the single-board computer (556) could be replaced with a microcontroller, digital signal processor, etc.

The electrodes (550) of FIG. 5 are attached to the user to acquire their EEG signal. The + and − electrodes are the inputs to the EEG amplifier and the COM electrode is used to bring the reference point of the EEG amplifier to the same electrical potential as the user. Many EEG based devices use proprietary electrodes designed specifically for their devices. The following work well: NeoTrace Kitty Cat Electrode, Kendall-LTP part number 1052NPSM, which is a self stick electrode with a solid gel adhesive hydrogel and a pre-attached lead wire with 1.5 mm safety socket termination.

Electroencephalographic (EEG) amplifier and filtering (552) comprise an integrated EEG amplifier module. This module amplifies and filters the EEG signal from electrodes (550). Most amplifier modules contain more than one channel. Depending on the number of channels required by the desired wake/sleep determination means (assuming EEG based), the + and − inputs of each unused amplifier channel should be shorted together and tied to COM to prevent the unused channels from introducing noise into the active channels. If the output of the EEG amplifiers (552) is an analog signal, then a data acquisition card (554) is needed to digitize the analog signal. Single board computers (556) are typically used in embedded applications.

The illustrated system also includes a liquid crystal display (LCD) with keypad (558). This is used as both an output device (display and backlight) and an input device (keypad) so that the user can interact with this system. The system may further include a speaker (560) as an audio output device.

In some instances, the main power supply for the system (564), may not produce the necessary voltages to operate the EEG amplifiers. Furthermore, many digital devices are connected to the power supply (564), and these devices tend to introduce a considerable amount of electrical noise into the power system. The EEG amplifiers may need to be isolated from this electrical noise either though filtering or adding a separate power supply for the analog amplifiers. Thus, the system may optimally also include an EEG power supply (562).

The system has a medically isolated power supply (564). This is the main system power supply. Since the system requires a low impedance electrical connection to the user (550), it is advisable to use a medically isolated power supply.

Finally, it is noted that a body wearable device would be functionally similar to that of the system of FIG. 5, but with different miniaturized hardware. Also, a body wearable system may also include a vibrating alert and would be battery operated. It may also include an in-bed sensor.

While the present invention has been described in relation to preferred embodiments, those skilled in the art may develop variations in the details thereof without departing from the principles of the invention. Accordingly, the appended claims are intended to be construed to cover all equivalents falling within the scope and spirit of the invention.

What is claimed is:

1. An automated system for facilitating the implementation of Behavioral Therapy that acquires and analyzes information indicative of a user's wake and sleep state to improve the user's sleep or sleep hygiene, comprising:
   means for passively acquiring information indicative of the user's wake and sleep state; and
   means for implementing steps of the Behavioral Therapy utilizing the user's wake and sleep state information.
2. The system of claim 1 in which the Behavioral Therapy comprises Stimulus Control Therapy, Sleep Restriction Therapy, Relaxation Therapy, Cognitive Behavioral Therapy for Insomnia, Behavioral Therapy for Insomnia, and combinations of two or more of Stimulus Control Therapy, Sleep Restriction Therapy, Relaxation Therapy, Cognitive Behavioral Therapy for Insomnia, and Behavioral Therapy for Insomnia.

3. The system of claim 1 including means for choosing the Behavioral Therapy to be implemented for a user based on the user's personal wake and sleep information.

4. The system of claim 1 in which information indicative of user's sleep/wake state is taken from the group consisting of: EEG, EMG, PAT, systolic upstroke time, ECG/EKG, EOG, oximetry, heart rate variations, heart rhythm variations, actigraphy, body movement, GSR, respiratory changes, respiratory variability, eye movements, and combinations of two or more of these means for passively determining information indicative of the user's wake and sleep state.

5. The system of claim 1 including Drug Therapy in conjunction with Behavioral Therapy.

6. The system of claim 1 in which active means for determining the wake and sleep state are used to supplement the means for passively determining information indicative of the user's wake and sleep state.

7. The system of claim 1 in which the Behavioral Therapy is Stimulus Control Therapy including means for implementing the Stimulus Control Therapy using the following rules:
   a) never alert a user while they are asleep,
   b) alert a user only when at least a first predetermined number of contiguous of wake epochs are achieved, and
   c) if any sleep of at least the second predetermined number of contiguous epochs is achieved, the maintenance flag is set and if any sleep of at least the second predetermined number of contiguous epochs is not achieved, the maintenance is not set whereby
   if maintenance flag is set, examine a past third predetermined number of epochs and if the user was awake for at least a fourth predetermined number of epochs out of the past third predetermined number of epochs, alert the user, but
   if the maintenance flag is not set and if there is no sleep of at least a fifth predetermined number of contiguous epochs within a first period of trying to fall asleep, then alert the user upon a lapse of the first period; and
   if the maintenance flag is not set and there is a contiguous sleep period contained within the first period of trying to fall asleep that is greater than or equal to the fifth predetermined number of epochs but less than the second predetermined number of epochs, then inhibit the alert for an additional period.

8. The method of claim 7 in which an epoch is about 30 seconds, the first predetermined number of contiguous wake epochs is 2, and the second predetermined number of contiguous epochs is 20 epochs, the third predetermined number of contiguous epochs is 30 epochs, the fourth predetermined number of epochs is 28 epochs; the fifth predetermined number of contiguous epochs is 10 epochs; the first period is 40 epochs, and the additional period is 20 epochs.

9. The system of claim 1 in which the means for implementing steps of the Behavioral Therapy comprises optimizing Behavioral Therapy parameters for a user based upon the user's wake and sleep information.

10. An apparatus for facilitating the implementation of Behavioral Therapy for a user seeking to improve the user's sleep or sleep hygiene comprising:
   means for processing information which is indicative of the user's wake and sleep state;
   means for implementing the Behavioral Therapy utilizing the wake and sleep state information.

11. The system of claim 10 in which means for processing information which is indicative of the user's wake and sleep state is taken from the group consisting of: EEG, EMG, PAT, systolic upstroke time, ECG/EKG, EOG, oximetry, heart rate variations, heart rhythm variations, actigraphy, body movement, GSR, respiratory changes, respiratory variability, eye movements, and combinations of two or more of these means for passively determining information indicative of the user's wake and sleep state.

12. The apparatus of claim 10 in which the Behavioral Therapy is Stimulus Control Therapy comprising:
   means for determining whether the user gets out of the bed in accordance with the rules of the Stimulus Control Therapy; and
   means for alerting the user to leave the bed in accordance with the rules of Stimulus Control Therapy.

13. The apparatus of claim 12 in which the alerting means are chosen from the group consisting of: a text display of warning conditions, text display of instructions or information, a display backlight, a blinking light, an audible indication, a tactile indication, a synthesized or recorded voice, a low level electrical stimulus and an aroma generated by appropriate device.

14. The apparatus of claim 12 including user-controlled means for canceling the alerting means.

15. The apparatus of claim 12 including a visual or audible presentation of instructions or information.

16. The apparatus of claim 12 including a means for providing an indication to the user after the user has been in bed for a recommended length of time.

17. The apparatus of claim 10 in which the Behavioral Therapy is Sleep Restriction Therapy comprising:
   means for calculating program parameters including a sleep period for the upcoming sleep session based on previously acquired wake and sleep state information in accordance with the rules of Sleep Restriction Therapy;
   means for determining whether the user has completed the sleep period; and
   means for displaying the calculated program parameters to the user for the upcoming sleep session.

18. The apparatus of claim 17 including means enabling the user to review and adjust the program parameters after display of such parameters for an upcoming sleep session.

19. The apparatus of claim 10 in which the Behavioral Therapy is chosen from the group consisting of Stimulus Control Therapy, Sleep Restriction Therapy, Relaxation Therapy, Cognitive Behavioral Therapy for Insomnia, Behavioral Therapy for Insomnia, and combinations of two or more of Stimulus Control Therapy, Sleep Restriction Therapy, Relaxation Therapy, Cognitive Behavioral Therapy for Insomnia, and Behavioral Therapy for Insomnia.

20. The apparatus of claim 10 including means permitting the user to review and adjust system settings chosen from the group consisting of time, age, sleep goals, alert preferences, language, setup parameters, and display preferences.

21. The apparatus of claim 10 in which the Behavioral Therapy is optimized for each user based upon the user's wake and sleep state information and/or wake and sleep state history.

22. The apparatus of claim 10 including means permitting the user to review information previously acquired by the apparatus.

23. The apparatus of claim 10 including means for computing the user's sleep statistics based on the user's previous wake and sleep state history.

24. The apparatus of claim 10 in which an indication of whether the user is in bed or not is acquired along with the wake and sleep state information.

25. The apparatus of claim 10 in which there is a means for turning off any alert and a means to display the user's current sleep statistics when a determination is made that the user is no longer in bed.

26. The apparatus of claim 10 in which there is a means for turning off any alert and a means of providing the user with sleep instructions when a determination is made that the user is no longer in bed.

27. The apparatus of claim 10 includes a means to allow the user to specify a predetermined wakeup time.

28. The apparatus of claim 10 in the form of a single portable unit wearable by the user.

29. The apparatus of claim 10 including means for calculating a time interval corresponding to the highest likelihood of being able to sleep to assist the user in planning the user's sleep.

30. The apparatus of claim 29 including means for informing the user as the user approaches the time interval corresponding to the highest likelihood of sleeping.

* * * * *

UNITED STATES PATENT AND TRADEMARK OFFICE
CERTIFICATE OF CORRECTION

PATENT NO. : 8,512,221 B2  
APPLICATION NO. : 12/639201  
DATED : August 20, 2013  
INVENTOR(S) : Richard Frederic Kaplan et al.

Page 1 of 1

It is certified that error appears in the above-identified patent and that said Letters Patent is hereby corrected as shown below:

On the title page item 75 the name of the first-named inventor is incorrectly spelled on the issued Letters Patent as displayed below:

Name as it appears on Letters Patent: "Kaplan Frederic Kaplan"

Correct name to appear on corrected Letters Patent: "Richard Frederic Kaplan"

Signed and Sealed this  
Fifteenth Day of October, 2013

Teresa Stanek Rea  
*Deputy Director of the United States Patent and Trademark Office*